United States Patent
Morrison

(10) Patent No.: US 6,340,467 B1
(45) Date of Patent: *Jan. 22, 2002

(54) SOLID AND SEMI-SOLID HYDROCARBON GELS AND USES THEREOF

(75) Inventor: David S. Morrison, The Woodlands, TX (US)

(73) Assignee: Pennzoil Products Company, Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/803,142

(22) Filed: Feb. 19, 1997

Related U.S. Application Data

(60) Provisional application No. 60/011,863, filed on Feb. 20, 1996.

(51) Int. Cl.[7] .................................................. A01N 25/00
(52) U.S. Cl. ........................ 424/405; 424/484; 424/486
(58) Field of Search .......................... 524/474; 514/787, 514/788.1; 424/405, 484, 486

(56) References Cited

U.S. PATENT DOCUMENTS

| | | | | |
|---|---|---|---|---|
| 4,164,563 A | * | 8/1979 | Chang | 514/10 |
| 4,164,564 A | * | 8/1979 | Chen | 514/788.1 |
| 4,369,284 A | | 1/1983 | Chen | 524/476 |
| 5,221,534 A | * | 6/1993 | DesLauriers et al. | 424/78.03 |
| 5,508,334 A | * | 4/1996 | Chen | 524/474 |
| 5,897,869 A | * | 4/1999 | Roulier et al. | 514/788.1 |

FOREIGN PATENT DOCUMENTS

| | | | |
|---|---|---|---|
| EP | 058022 | 8/1982 | H01B/7/28 |
| EP | 0224389 | 6/1987 | |
| GB | 1344368 | 1/1974 | C08F/43/00 |
| JP | Sho 62-38166 | 8/1994 | |
| WO | WO 88/00603 | 1/1988 | |
| WO | WO 91/05014 | 4/1991 | C08L/53/02 |
| WO | WO 94/12190 | 6/1994 | A61K/31/74 |

* cited by examiner

Primary Examiner—Thurman K. Page
Assistant Examiner—Robert M. Joynes
(74) Attorney, Agent, or Firm—McDermott, Will & Emery

(57) ABSTRACT

A solid or semi-solid hydrocarbon gel comprising:
  a) a solid or semi-solid hydrocarbon; and
  b) at least one block copolymer selected from the group consisting of:
    a triblock copolymer;
    a radial block copolymer;
    a multiblock copolymer
    a diblock copolymer; and
    mixtures of these polymers.

The hydrocarbon gel is useful as an ointment, balm or salve for wounds. Medicinal ingredients may be included in the hydrocarbon gel for application of such ingredients to wounds, burns or injuries.

18 Claims, No Drawings

SOLID AND SEMI-SOLID HYDROCARBON GELS AND USES THEREOF

This application claims the benefit of U.S. Provisional Application Ser. No. 60/011,863, filed Feb. 20, 1996.

FIELD OF THE INVENTION

This invention relates to solid hydrocarbon gel products and more particularly relates to solid hydrocarbon gel products and novel uses thereof in various applications.

BACKGROUND ART

Various types of gel products are known in the art. U.S. Pat. No. 5,221,534 of Applicants' Assignee, for example discloses gel compositions which contain one or more health and beauty aid components wherein the gel comprises a hydrocarbon oil and a blend of at least two different polymers selected from the group consisting of diblock and triblock polymers. The hydrocarbon oils disclosed in this patent are indicated as having characteristics which would cause them to remain liquid at temperatures ranging from 0° C. up to about 200° C. for almost all applications.

U.S. Pat. No. 4,164,563 to Chang discloses compositions for topical application to the skin which are indicated as being greasy occlusive viscous bases comprising a mixture of from 40–90% of a greasy viscous base and from 10–60% of a solid non-irritating ointment forming powder. Other ingredients such as colorants can also be included in the composition. The composition can also contain a thickening agent which can be an unvulcanized elastomeric block polymer.

International Application PCT No. W88/00603, published Jan. 28, 1988 by Francis et al. discloses block copolymers which are described as gels or gel liquid extended polymer compositions which can comprise a mixture of a block copolymer containing relatively hard blocks and relatively elastomeric blocks. Such block copolymers include styrene-diene block copolymers which can be diblock or triblock copolymers. Extender liquids mentioned in this patent are hydrocarbon oils such as paraffinic or napthenic oils, synthetic oils such as polybutene or polypropylene, and mixtures.

Published European Patent Application No. 224,389 discloses styrene-diene block copolymer compositions which comprise a mixture of triblock copolymers and a hydrocarbon oil. These materials are indicated as being useful as sealing materials.

The present invention provides solid hydrocarbon products which is are novel composition having uses unexpected in view of the prior art.

SUMMARY OF THE INVENTION

It is accordingly one object of the present invention to provide a novel, solid hydrocarbon gel product and articles of manufacture made therefrom.

A further object of the invention is to provide a method for the preparation of useful solid hydrocarbon gel products.

Other objects and advantages of the invention will become apparent as the description thereof proceeds.

In satisfaction of the foregoing objects and advantages, the present invention provides a solid hydrocarbon gel product, processes of making same and articles of manufacture made therefrom. The solid hydrocarbon gel comprises a) a solid or semi-solid hydrocarbon, and b) at least one block copolymer selected from the group consisting of:

1) a triblock copolymer;
2) a radial block copolymer;
3) a multi-block copolymer;
4) a diblock copolymer; or
5) mixtures of these polymers.

DESCRIPTION OF THE INVENTION

The present invention is directed to a novel, solid hydrocarbon gel product which finds application in many areas to produce novel and unexpected products. The product, which is a solid or semi-solid product at room temperature (25° C.), is produced from a composition comprising a polymer, a solid or a semi-solid hydrocarbon product and optionally an oil. The solid hydrocarbon gel therefore comprises: a) a solid or semi-solid hydrocarbon, and b) at least one block copolymer selected from the group consisting of:

1) a triblock copolymer;
2) a radial block copolymer;
3) a multi-block copolymer;
4) a diblock copolymer; and
5) mixtures of these polymers.

The solid or semi-solid hydrocarbon is a hydrocarbon material which is at least semi-solid and preferably solid at room temperature, that is about 25° C. Examples of suitable solid hydrocarbons include paraffin wax, petrolatum, synthetic waxes, mineral (paraffins) waxes, vegetable oil waxes, polyethylene waxes, microcrystalline waxes, natural waxes such as carnauba, beeswax and the like. Therefore, this solid hydrocarbon includes both petroleum based and non-petroleum based solid hydrocarbons.

It is also optional to include in the composition a liquid hydrocarbon such as a white mineral oil to modify the softening point of the gel. Resins may also be included in for this purpose.

In the composition, the total polymer content of the solid hydrocarbon gel will range from greater than 0 to about 50% by weight and preferably will range from about 0.05 up to about 35 wt. %. Especially preferred compositions will contain about 1 to 25 wt. % of total polymer content.

The solid hydrocarbon may accordingly comprise from greater than about 0 to about 99% by weight of the composition and preferably will range from about 20 to 95% by weight.

As indicated, oils, resins and the like can be added to modify the softening point of the gel. When such oils or resins are added, they are added in an amount ranging from about 5 to 75% by weight. Additional hydrocarbon based materials such as esters may also be included in the solid gel in amounts of up to about 75%. Other functional ingredients, for example, antioxidants, stabilizers, fragrances or colorants and the like may also be incorporated in amounts of about 0.1 to 10 wt. %.

The gel is prepared by heating the solid or semi-solid hydrocarbon under atmospheric conditions so as to form a melt and then adding the polymer thereto with agitation. The heating and agitation are maintained until the polymer is dissolved in the hydrocarbon.

Any additional materials or ingredients may then optionally be added, preferably while the gel is cooling.

The polymeric components used in the present invention are preferably of the diblock or triblock type and more preferably are either triblock polymers alone or mixtures of diblock and triblock polymers. When mixtures of diblock copolymers and triblock copolymers are used as the polymer component, the mixture may comprise from about 0.1 to 99.9% wt. % of diblock copolymers to about 99.9 to 0.1 wt. % of triblock copolymers.

Each of the diblock, triblock, radial block and/or multiblock copolymers used in the invention contains at least two thermodynamically incompatible segments. By the expression thermodynamically incompatible with respect to the polymers, it is meant that the polymer contains at least two incompatible segments, for example, at least one hard and one soft segment. In general, in a triblock copolymer, the ratio of segments is one hard, one soft, one hard or an A-B-A copolymer. Diblock copolymers, on the other hand, are of the A-B type and sequential with respect to hard and soft segments. The multiblock and radial block copolymers can contain any combination of hard and soft segments, provided that there are both hard and soft characteristics. Such polymers are fully described in U.S. Pat. No. 5,221,534.

Commercially available thermoplastic rubber type polymers which are especially useful in forming the compositions of the present invention are sold under the trademark Kraton® by Shell Chemical Company. The Kraton® rubber polymers are described as elastomers which have an unusual combination of high strength and low viscosity and a unique molecular structure of linear diblock, triblock and radial copolymers. Each molecule of the Kraton® rubber is said to consist of block segments of styrene monomer units and rubber monomer and/or comonomer units. Each block segment may consist of 100 or more monomer or comonomer units. The most common structure for the triblock copolymer is the above-mentioned linear ABA block type; styrene-butadiene-styrene (SBS) and styrene-isoprene-styrene (SIS), which is the Kraton® D rubber series.

A second polymer of this general type is the Kraton® G series. This copolymer comprises a styrene-ethylenebutylene-styrene type (S-EB-S) structure. The Kraton® G series is preferred in the practice of the invention, as the copolymers of this series are hydrogenated and thus more thermally stable; that is, decomposition is less likely to occur during blending of the G series polymers with the hydrocarbon (the D series polymers having unsaturation within the rubber block).

The ABA structure of the Kraton® rubber molecule has polystyrene end blocks and elastomeric midblocks. This series of polymers is indicated as being a compounding ingredient or additive in adhesives, sealants and coatings, asphalt modification for roads and roofing, polymer modification, thermoset modifications, and oil modification including use as viscosity index improvers, greases and gels.

A preferred triblock polymer is a triblock polymer of the Kraton® G type, in particular Kraton® G-1650, Kraton®-1650 is an SEBS triblock copolymer which has a specific gravity of about 0.91, and is said to have a tensile strength of about 500 psi as measured by ASTM method D-412-tensile jaw tester separation speed 10 in/min. The styrene to rubber content of Kraton® G-1650 is said by the manufacturer to be about 29:71, and the Brookfield viscosity is about 8000 (toluene solution, cps at 77° F., 25% w). The Shore A hardness is about 75.

The diblock polymers include the AB type such as styrene-ethylenepropylene (S-EP) and styrene-ethylenebutylene (S-EB), styrene-butadiene (SB) and styrene-isoprene (SI). A preferred diblock copolymer is Kraton® G-1702.

The solid hydrocarbon gels of the invention are useful in several areas. For example, they are useful as hydrocarbon fuel for candles, as the base for deodorant and insect repellant sticks, air-freshener sticks and other cosmetic and non-cosmetic products. In such compositions, an active ingredient would be included in the composition. The gels may also be used as a hair treatment. The solid gels of the invention have a lower tendency to melt and therefore a greater tendency to remain where applied (i.e., not run or drip), particularly during periods of excessive body heat.

In a further embodiment, a solid hydrocarbon gel of the invention may be used as a topical product such as an ointment, balm or salve where it is placed directly on the skin wound or it may be placed by the user on a dressing such as a bandage or gauze which is then placed on the wound. The gel may also be manufactured as part of the wound dressing.

The solid hydrocarbon gel can be applied to lesions, lacerations, tears, gashes, incisions, abrasions, burns, scrapes, scratches and the like when used in wound care.

In a further embodiment, the solid hydrocarbon gel may also contain from about 0.1 to about 10.0 wt. % of drugs or medicines such as antibacterials, antibiotics, antifungals, antivirals, anesthetics, therapeutic ingredients and other ingredients which would keep a wound site sterile and free of infection. Medicinal materials which may be included in the gel include pharmaceutical products, either prescription or nonprescription, herbal products and the like.

Other ingredients which may also be incorporated into the gel comprise from about 0.1 to about 10 wt. % of vitamins, anti-oxidants, liquid or solid emollients to improve skin feel (such as esters and silicones), agents to promote blood clotting via physiological means or via physical means, agents to promote or speed healing, agents to soak up fluids from the wound site, and additives to prevent a bandage from sticking to the skin or wound site.

The solid hydrocarbon gels may also include from about 0.1 up to 50 wt. % of additional ingredients such as various hydrocarbons added solely to alter the physical properties of the gel. For example, various waxes can be added such as carnauba wax, beeswax or candellia wax for the purpose of varying the melting point or softening point of the gel. Liquids which are hydrocarbon soluble such as white mineral oil or other hydrocarbons may be added for this purpose as well.

An advantage of the products of this invention is the tendency of the product to remain where it is applied. That is, it will not run or drip, particularly during periods of excessive body heat. Also, this tendency to stay solid or semisolid at elevated temperatures is useful for keeping any additives in the gel from settling out or separating during the manufacturing process and during the gels resinous time on the skin.

The gels may also find application in care of other skin problems such as warts or acne and can be used for holding peroxides on the skin to promote acne healing and for keeping ingredients, for example, keratolytics, such as salicylic acid in place to help dissolve warts or calluses.

EXAMPLES

The following Table 1 presents several formulations which exemplify the invention.

The formulations listed in Table 1 were made using ingredients Drakeol® 7, (white mineral oil), Kraton® 1702 diblock copolymer, Kraton® 1650 triblock copolymer and/or Kraton® 1726 triblock copolymer. These Kraton® polymers are available from Shell Chemical Company.

TABLE 1

| Petrolatum, wt % | Drakeol 7® Mineral oil, wt % | Kraton® 1702 Diblock copolymer, wt % | Kraton® 1650 Triblock copolymer, wt % | Kraton® 1726 Triblock copolymer, wt % |
|---|---|---|---|---|
| 95.25 | — | 4.50 | 0.25 | — |
| 93.10 | — | 6.50 | 0.40 | — |
| 92.00 | — | 7.60 | 0.40 | — |
| 91.30 | — | 8.30 | 0.40 | — |
| 91.40 | — | 0.10 | 8.50 | — |
| 85.00 | — | 15.00 | — | — |
| 85.00 | — | — | 15.00 | — |
| 85.00 | — | — | — | 15.00 |
| 20.00 | 74.48 | 5.20 | 0.32 | — |
| 50.00 | 46.55 | 3.25 | 0.20 | — |
| 80.00 | 18.62 | 1.30 | 0.08 | — |
| 20.00 | 73.60 | 6.08 | 0.32 | — |
| 50.00 | 46.00 | 3.80 | 0.20 | — |
| 80.00 | 18.40 | 1.52 | 0.08 | — |
| 20.00 | 73.04 | 6.64 | 0.32 | — |
| 50.00 | 45.65 | 4.15 | 0.20 | — |
| 80.00 | 18.26 | 1.66 | 0.08 | — |
| 92.00 | — | 7.60 | 0.40 | — |
| 93.10 | — | 6.50 | 0.40 | — |
| 95.25 | — | 4.50 | 0.25 | — |

As noted in Table 1, the formulations include those which include an oil component and those which do not include an oil component. The formulations of Table 1 also exemplify solid gels which contain triblock copolymers alone and mixtures of diblock and triblock copolymers.

The invention has been described with a reference to certain preferred embodiments. However, its obvious variations thereon will become apparent to those skilled in the art. The invention is not to be considered as limited thereto.

What is claimed is:

1. A solid or semi-solid hydrocarbon gel that does not run or drip at excessive body heat consisting essentially of:
   a) a synthetic or natural solid or semi-solid hydrocarbon that is solid or semi-solid at about 25° C. selected from the group consisting of paraffin wax, petrolatum, mineral waxes, vegetable oil waxes, polyethylene waxes, microcrystalline waxes, carnauba, beeswax, and mixtures thereof; and said hydrocarbon having dissolved therein;
   b) at least one block copolymer selected from the group consisting of:
      a triblock copolymer;
      a radial block copolymer
      a multiblock copolymer;
      a diblock copolymer; and
      mixtures of these polymers;
   wherein said hydrocarbon gel comprises from about 1% to about 50% by weight of said polymer, and a sufficient amount of said hydrocarbon to maintain the solid or semi-solid gel form, said amount containing from greater than 20% to about 95% by weight of solid or semi-solid hydrocarbon, and wherein said triblock copolymers are selected from the group consisting of linear ABA block copolymers, styrene-butadiene-styrene(SBS) block copolymers, styrene-isoprene-styrene(SIS) block copolymers, and styrene-ethylenebutylene-styrene(S-EB-S) block copolymers, and said diblock copolymers are selected from the group consisting of styrene-ethylenepropylene(S-EP), styrene-ethylenebutylene(S-EB), styrene-butadiene (SB), and styrene-isoprene(SI) block copolymers, said gel further optionally containing:
   one or more additives selected from the groups consisting of:
   1) functional ingredients containing about 0.1 to 10 weight percent of antioxidants, stabilizers, fragrances or colorants;
   2) an effective amount of antibacterials, antibiotics, antifungals, antivirals, anesthetics, therapeutic ingredients or herbal products; and
   3) an effective amount of vitamins, anti-oxidants, liquid or solid emollients, blood clotting agents, healing agents, adsorbents for wounds, or additives to prevent a bandage from sticking to the skin or a wound site;
   wherein said gel will not run or drip during periods of excessive body heat, and said additives will not settle or separate out of the gel.

2. A solid or semi-solid hydrocarbon gel according to claim 1, wherein the block copolymer comprises a mixture of a triblock copolymer and a diblock copolymer.

3. A solid or semi-solid hydrocarbon gel according to claim 1, wherein said at least one block copolymer comprises a triblock copolymer.

4. A solid or semi-solid hydrocarbon gel according to claim 1, wherein said at least one block copolymer comprises a diblock copolymer.

5. A solid or semi-solid hydrocarbon gel according to claim 1, which also comprises one or more of said antioxidants, stabilizers, fragrances or colorants.

6. A solid or semi-solid hydrocarbon gel according to claim 1, wherein the gel also comprises about 0.1 to about 10 weight percent of said one or more antibacterial agents, antibiotics, antifungal agents, antiviral agents, anesthetics, vitamins, antioxidants, emollients, blood clotting agents, healing agents, adsorbents, or additive to prevent a bandage from sticking to the skin or a wound site.

7. A topical composition for treating a wound, burn or injury which comprises a solid or semi-solid hydrocarbon gel that does not run or drip at excess body heat, said composition containing a gel formed from:
   a) a synthetic or natural solid or semi-solid hydrocarbon that is solid or semi-solid at about 25° C. selected from the group consisting of paraffin wax, petrolatum, mineral waxes, vegetable oil waxes, polyethylene waxes, microcrystalline waxes, carnauba, beeswax, and mixtures thereof; and said hydrocarbon having dissolved therein;
   b) at least one block copolymer selected from the group consisting of:
      a triblock copolymer;
      a radial block copolymer
      a multiblock copolymer;
      a diblock copolymer; and
      mixtures of these polymers;
   wherein said hydrocarbon gel comprise from about 1% to about 50% by weight of said polymer content, and a sufficient amount of said hydrocarbon to maintain the solid or semi-solid gel form, said amount containing from greater than 20% to about 95% by weight of solid or semi-solid hydrocarbon, and wherein said triblock copolymers are selected from the group consisting of linear ABA block copolymers, styrene-butadiene-styrene(SBS) block copolymers, styrene-isoprene-styrene(SIS) block copolymers, and styrene-ethylenebutylene-styrene(S-EB-S) block copolymers, and said diblock copolymers are selected from the group consisting of styrene-ethylenepropylene(S-EP), styrene-ethylenebutylene(S-EB), styrene-butadiene (SB), and styrene-isoprene(SI) block copolymers;

and further containing one or more additives selected from the group consisting of:
1) about 0.1 to about 10 weight percent of antibacterials, antibiotics, antifungals, antivirals, anesthetics, therapeutic ingredients or herbal products; and
2) about 0.1 to about 10 weight percent of vitamins anti-oxidants, liquid or solid emollients, blood clotting agents, healing agents, adsorbents for wounds, or additives to prevent a bandage from sticking to the skin or a wound site; and optionally one or more functional ingredients containing an effective amount of antioxidants, stabilizers, fragrances or colorants; wherein said gel will not run or drip during periods of excessive body heat, and said additives will not settle or separate out of the gel.

8. A composition according to claim 7, wherein the block copolymer comprises a mixture of a triblock copolymer and a diblock copolymer.

9. A composition according to claim 7, wherein said at least one block copolymer comprises a diblock copolymer.

10. A composition according to claim 7, wherein said at least one block copolymer comprises a triblock copolymer.

11. A composition according to claim 7, which also comprises an effective amount of one or more antioxidants; stabilizers, fragrances or colorants.

12. A composition according to claim 7, wherein the hydrocarbon comprises from about 20 to 95% by weight of the composition, and the copolymer comprises from about 1 to 25% by weight of the composition.

13. A solid or semi-solid hydrocarbon gel that does not run or drip at excessive body heat consisting essentially of:
    a) a synthetic or natural solid or semi-solid hydrocarbon that is solid or semi-solid at about 25° C. selected from the group consisting of paraffin wax, petrolatum, mineral waxes, vegetable oil waxes, polyethylene waxes, microcrystalline waxes, carnauba, beeswax, and mixtures thereof; and said hydrocarbon having dissolved therein;
    b) at least one block copolymer selected from the group consisting of:
        a triblock copolymer;
        a radial block copolymer
        a multiblock copolymer;
        a diblock copolymer; and
        mixtures of these polymers;
    wherein said hydrocarbon gel comprises from about 1% to about 50% by weight of said polymer, and a sufficient amount of said hydrocarbon to maintain the solid or semi-solid gel form, said amount containing from greater than 20% to about 95% by weight of solid or semi-solid hydrocarbon, and wherein said triblock copolymers are selected from the group consisting of linear ABA block copolymers, styrene-butadiene-styrene(SBS) block copolymers, styrene-isoprene-styrene(SIS) block copolymers, and styrene-ethylenebutylene-styrene(S-EB-S) block copolymers, and said diblock copolymers are selected from the group consisting of styrene-ethylenepropylene(S-EP), styrene-ethylenebutylene(S-EB), styrene-butadiene (SB), and styrene-isoprene(SI) block copolymers; and
    (c) one or more additives selected from the group consisting of:
        a peroxide and a keratolytic;
    wherein said gel will not run or drip during periods of excessive body heat, and said additives will not settle or separate out of the gel.

14. A gel according to claim 13, wherein the additive is a peroxide.

15. A gel according to claim 13, wherein the additive is a keratolytic.

16. A gel according to claim 15, wherein the keratolytic is salicylic acid.

17. A gel according to claim 1, wherein the solid or semi-solid hydrocarbon is a solid at about 25° C.

18. A gel according to claim 7, wherein the solid or semi-solid hydrocarbon is a solid at about 25° C.

* * * * *